United States Patent
Walimbe et al.

(10) Patent No.: US 8,260,025 B2
(45) Date of Patent: Sep. 4, 2012

(54) METHODS AND APPARATUS FOR GENERATING AND ARCHIVING X-RAY FLUOROSCOPY IMAGES

(75) Inventors: Vivek Walimbe, Pewaukee, WI (US); Romain Areste, Milwaukee, WI (US); Kadri Jabri, Waukesha, WA (US); Jon Omernick, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 728 days.

(21) Appl. No.: 12/277,088

(22) Filed: Nov. 24, 2008

(65) Prior Publication Data

US 2010/0128955 A1    May 27, 2010

(51) Int. Cl.
*G06K 9/00* (2006.01)
*A61B 6/00* (2006.01)

(52) U.S. Cl. .................. 382/132; 382/131; 378/4

(58) Field of Classification Search .......... 382/131, 382/132; 378/42
See application file for complete search history.

(56) References Cited

U.S. PATENT DOCUMENTS

| | | | |
|---|---|---|---|
| 5,119,409 A * | 6/1992 | Nields et al. | 378/106 |
| 6,226,350 B1 * | 5/2001 | Hsieh | 378/98 |
| 6,278,765 B1 * | 8/2001 | Berliner | 378/98.12 |
| 6,332,014 B1 | 12/2001 | Boutenko et al. | |
| 6,437,306 B1 * | 8/2002 | Melen | 250/208.1 |
| 7,545,967 B1 * | 6/2009 | Prince et al. | 382/130 |
| 2006/0133564 A1 * | 6/2006 | Langan et al. | 378/8 |
| 2007/0003014 A1 * | 1/2007 | Boese et al. | 378/95 |
| 2007/0269019 A1 * | 11/2007 | Spahn | 378/207 |

* cited by examiner

*Primary Examiner* — Alexander H Taningco
(74) *Attorney, Agent, or Firm* — The Small Patent Law Group; Dean D. Small (57) ABSTRACT

Methods and apparatus for generating and archiving x-ray fluoroscopy images are provided. The method includes obtaining x-ray fluoroscopy data comprising a plurality of image frames and performing image enhancement, including motion correction, based on a subset of the acquired plurality of x-ray fluoroscopy image frames to generate a single enhanced x-ray image.

22 Claims, 7 Drawing Sheets

# METHODS AND APPARATUS FOR GENERATING AND ARCHIVING X-RAY FLUOROSCOPY IMAGES

BACKGROUND OF THE INVENTION

This invention relates generally to diagnostic imaging systems, and more particularly to x-ray fluoroscopy imaging systems.

Diagnostic imaging systems are used in many different applications. One type of diagnostic imaging system is an x-ray imaging system. Using an x-ray imaging system, x-ray fluoroscopy may be used to obtain real-time moving images of the internal structures of a patient using a fluoroscope. Fluoroscopy has many known uses in diagnostic and image-guided procedures, including general-purpose fluoroscopy, vascular imaging, etc. During some fluoroscopic imaging procedures a patient may have to be imaged a number of times to obtain images having diagnostically relevant information.

Moreover, in conventional fluoroscopy systems, the last frame of a fluoroscopy acquisition sequence is displayed on screen after radiation/exposure has been terminated. This feature is referred to as Last Image Hold (LIH). In these conventional systems, it is possible to save this last acquired fluoroscopy image frame as part of patient record. However, the image quality of the LIH is marginal for diagnostic purposes and/or including in patient record for future review.

Thus, because of the marginal and sometimes unacceptable image quality of fluoroscopy LIH for static image display, most radiologists acquire an additional/replacement high-dose radiography (RAD) exposure at the point (spatial/temporal) of interest. The RAD exposure provides improved image quality compared to a fluoroscopic LIH, for example, to record anatomical information, but with substantially higher dose. Additionally, accumulation of multiple RAD exposures may be needed and requires multiple repeats of the procedure due to the delay in transitioning from a user observation of the event under fluoroscopy to actual RAD exposure. Accordingly, the patient is exposed to additional radiation.

Accordingly, the typical image quality is poor for archiving fluoroscopic images as part of patient record. Also, the alternative approach of acquiring a RAD exposure to record anatomical information provides improved image quality, but typically requires higher dose.

BRIEF DESCRIPTION OF THE INVENTION

In accordance with one embodiment, a method for enhancing x-ray images is provided. The method includes obtaining x-ray fluoroscopy data comprising a plurality of image frames and performing image enhancement, including motion correction, based on a subset of the acquired plurality of x-ray fluoroscopy image frames to generate a single enhanced x-ray image.

In accordance with another embodiment, a method for enhancing and archiving x-ray images is provided. The method includes obtaining x-ray fluoroscopy data comprising a plurality of image frames and identifying at least one of the x-ray fluoroscopy image frames for enhancement based on a user input. The method further includes performing image enhancement, including motion-correction, using a subset of the x-ray fluoroscopy image frames, including the user identified image frame, to generate a single enhanced x-ray image corresponding to each of the identified x-ray fluoroscopy image frames.

In accordance with yet another embodiment, an x-ray fluoroscopy imaging system is provided that includes an x-ray generator configured to generate and emit low dose x-rays and an x-ray detector configured to detect low dose x-rays emitted from the x-ray generator after passing through an object to generate low dose x-ray fluoroscopy data. The x-ray fluoroscopy imaging system further includes a memory for storing the low dose x-ray fluoroscopy data from the x-ray detector and an image enhancement module configured to generate an enhanced x-ray image based on at least some of the acquired fluoroscopy image data, the enhanced x-ray image generated one of (i) automatically and (ii) based on a user input.

DETAILED DESCRIPTION OF THE INVENTION

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments of the invention provide methods and systems for generating enhanced images, for example, higher quality images from acquired lower quality (such as low dose) image data. Although the various embodiments are described in connection with an x-ray fluoroscopic imaging system, the systems and methods described herein may be used with different types of medical (e.g., magnetic resonance imaging, ultrasound imaging, computed-tomography imaging, etc.) and non-medical (e.g., non-destructive testing systems, such as airport screening) imaging systems.

Figure 1:
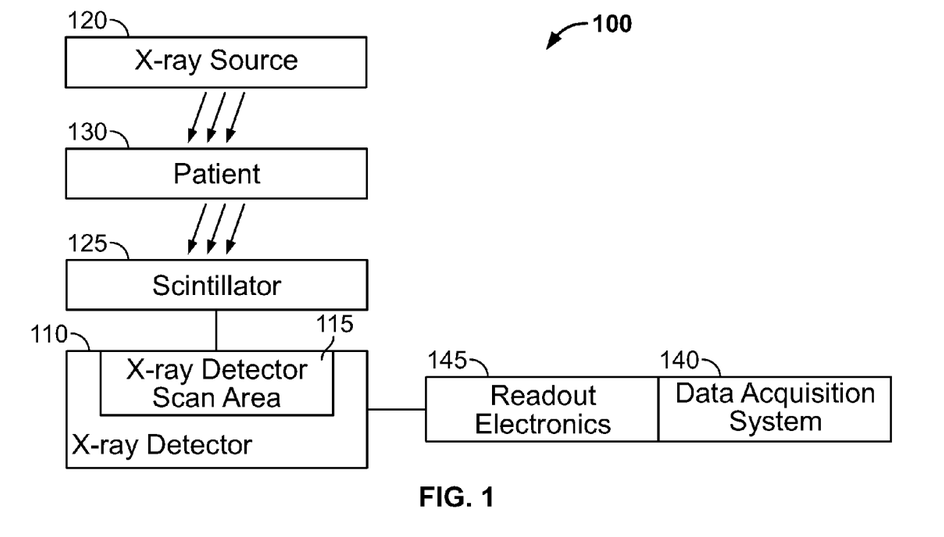
FIG. 1 is a block diagram of an imaging system formed in accordance with various embodiments of the invention.

FIG. 1 illustrates an imaging system 100 used in accordance with various embodiments of the invention. For purposes of illustration, the imaging system 100 is described as an x-ray system. The imaging system 100 generally includes an x-ray detector 110 having an array 115 of detector cells, an x-ray source 120 and a scintillator 125. An object, such as a patient 130 is positioned between the x-ray source 120 and the scintillator 125. The imaging system 100 also includes a data acquisition system 140 with readout electronics 145.

In one embodiment, the scintillator 125 includes a screen positioned in front of the detector 110. Alternatively, the detector 110 may be a flat-panel detector system such as an amorphous silicon flat panel detector or other type of digital x-ray image detector.

In operation, the patient 130 is positioned in the imaging system 100 for performing an imaging scan. For example, the x-ray source 120 may be positioned above the patient 130 or below the patient 130. The x-ray source 120 also may be moved between different positions around the patient 130. The scintillator 125 is positioned between the patient 130 and the x-ray detector 110. X-rays are transmitted from the x-ray source 120 through the patient 130 to the scintillator 125. The scintillator 125 emits light in response to the x-rays transmitted from the x-ray source 120 through the patient 130. The emitted light is transmitted to the x-ray detector 110 and the x-ray detector array 115. For example, light emitted by the scintillator 125 activates or discharges photodiodes in the detector array 115 to varying degrees. The readout electronics 145 may include a reference and regulation board (RRB) or other data collection unit. The RRB may accommodate and connect data modules to transfer data from the detector 110 to the data acquisition system 140. The read out electronics 145 transmit the data from the detector 110 to the data acquisition system 140. The data acquisition system 140 forms an image from the data and may store, display, and/or transmit the image. Preprocessing and processing functions also may be applied to the acquired image before and/or after storage, display, and/or transmission. For example, the various embodiments may generate an enhanced image from a plurality of acquired images as described in more detail below.

Figure 2:
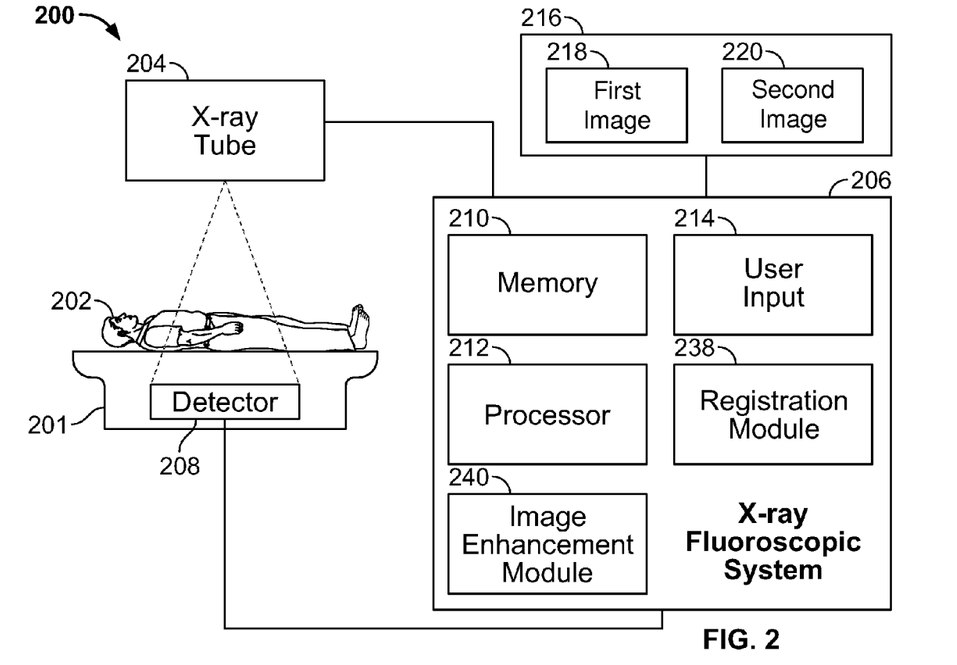
FIG. 2 is a block diagram of a fluoroscopic imaging system formed in accordance with various embodiments of the invention.

Various embodiments may be provided in connection with an x-ray fluoroscopic imaging system 200 (also referred to as a fluoroscope) as shown in FIG. 2. The x-ray fluoroscopic imaging system 200 may be used to obtain real-time moving images of the internal structures of a patient 202. The x-ray fluoroscopic imaging system 200 includes a table 201 or bed for supporting the patient 202. An X-ray tube 204 or other generator is connected to an x-ray fluoroscopic processing sub-system 206. As shown, the x-ray tube 204 is positioned above the patient 202, but it should be understood that the x-ray tube 204 may be moved to other positions with respect to the patient 202. A detector 208 is positioned opposite the x-ray tube 204 with the patient 202 therebetween. The detector 208 may be any known detector capable of detecting x-ray radiation.

The x-ray fluoroscopic processing sub-system 206 includes at least a memory 210, a processor 212 and at least one user input 214, such as a keyboard, trackball, pointer, touch panel, and the like. To acquire an x-ray image, the x-ray fluoroscopic processing sub-system 206 causes the x-ray tube 204 to generate x-rays and the detector 208 detects x-rays that pass through the patient 202 and impinge on the detector 208. Fluoroscopy may be accomplished by activating the x-ray tube 204 continuously or at predetermined intervals while the detector 208 detects corresponding emitted x-rays. One or more image(s) 218 and 220, for example, fluoroscopic x-ray images generated from the detected x-rays during a low dose scan may be displayed on a display 216 that may be configured to display a single image or more than one image at the same time. It should be noted that the images 218 and 220 acquired by x-ray fluoroscopic imaging system 200 may be acquired in any known manner.

The x-ray fluoroscopic processing subsystem 206 also may include a registration module 238, which may be a processor configured to process received image data to register the first and second images 218 and 220 with respect to each other. The x-ray fluoroscopic processing subsystem 206 also may include an image enhancement module 240 to generate enhanced fluoroscopic images (e.g., higher quality images from low dose scans) for display, archiving and/or printing.

Figure 3:
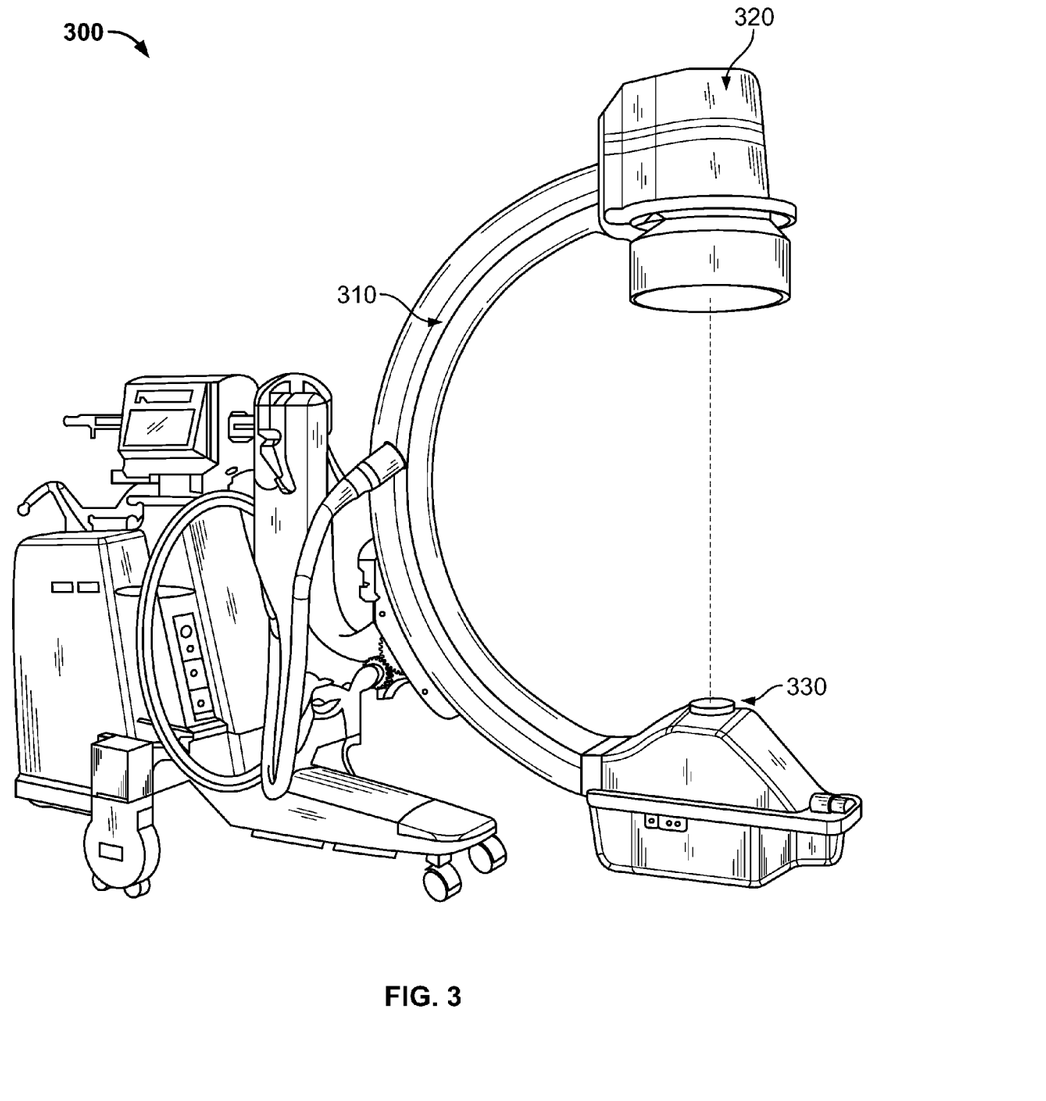
FIG. 3 is a perspective view of a mobile imaging system formed in accordance with various embodiments of the invention.

The imaging system 100 may be implemented as a non-mobile (as shown in FIG. 2) or mobile imaging system as shown in FIG. 3. For example, FIG. 3 illustrates a mobile imaging system 300 that may be used in accordance with an embodiment of the present invention and configured as a mobile fluoroscopic imaging system. The mobile imaging system 300 may include some or all of the imaging system 100 or a similar system. The mobile imaging system 300 includes a C-arm 310, an energy source 320 (e.g., an x-ray energy source), an image acquisition device 330 (e.g., a detector or camera) and a positioning surface 340 (e.g., a patient positioning table). Optionally, the C-arm 310 may be, for example, an L-arm, an O-arm, a C-gantry, and/or other positioning element. Also, the imaging system 100 may be implemented as a stand-alone % or wall mounted unit.

In operation, an object may be positioned on the positioning surface 340. Image data related to the object may be obtained at the image acquisition device 330 after energy from the energy source 320 has irradiated the object. Thus, fluoroscopic ("fluoro") images (e.g., dye contrast injected images) may be acquired of patient or a region of interest of the patient.

Various embodiments of the invention provide methods and systems to generate and store improved quality or enhanced images for fluoroscopy imaging. In particular, at least one technical effect of the various embodiments is to improve the image quality for fluoroscopy image archiving that precludes the need for additional higher radiation exposures. The various embodiments also allow user configurable options to generate the improved quality or enhanced images.

Specifically, various embodiments of the invention use, for example, motion correction and/or temporal image accumulation/filtering for improving image quality in fluoroscopic images by reducing noise. In particular, individual fluoroscopic images are generally acquired at a substantially lower dose than a single higher radiation (RAD) exposure. The image noise in these low-dose fluoroscopy images is reduced by accumulating existing successive fluoroscopic images in a sequence, thus providing an output image with considerably less noise, at no additional dose to the patient. The need for additional RAD exposures is thereby precluded or reduced, which would otherwise be needed for including in, for example, the patient record.

Figure 4:
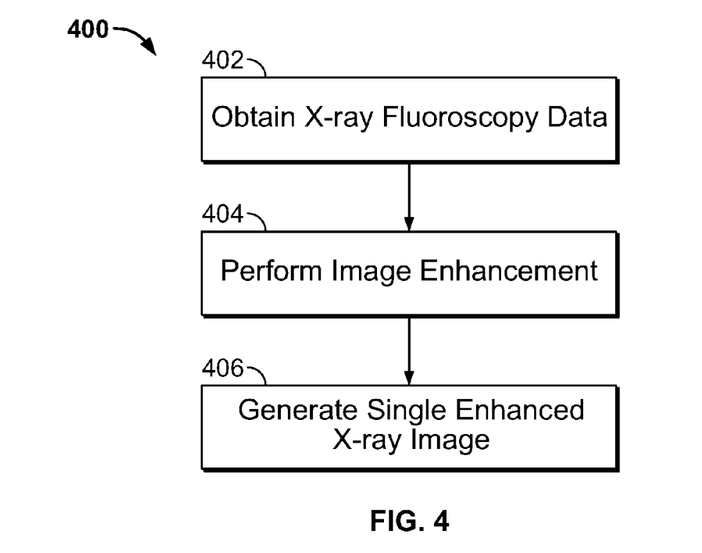
FIG. 4 is a flowchart of a method for enhancing x-ray images in accordance with various embodiments of the invention.

In accordance with various embodiments, a method 400 for enhancing x-ray images, such as fluoroscopic images, is shown in FIG. 4. The method 400 includes obtaining x-ray fluoroscopy data at 402. For example, a plurality of images or frames of x-ray fluoroscopic data may be obtained from a current imaging scan or from stored data acquired during a previous imaging scan. The x-ray fluoroscopy data generally includes a plurality of frames of data acquired using low dose x-ray scanning techniques as described in more detail herein. Thereafter, image enhancement is performed at 404, which may include performing motion correction based on a subset of the acquired plurality of frames of data. For example, correction for gross image misalignment due to detector panning motion and/or more precise or fine image correction due to patient movement as is known may be performed as described in more detail herein.

After the subset of image frames have been motion corrected, the motion corrected image frames are combined to generate a single enhanced x-ray image, for example, an x-ray fluoroscopic image having an enhanced image quality, such as improved anatomical landmarks. The motion corrected image frames may be combined in any known manner, for example, by averaging the image data in the image frames. Optionally, weighted temporal filtering of the motion corrected image frames may be performed.

Figure 5:
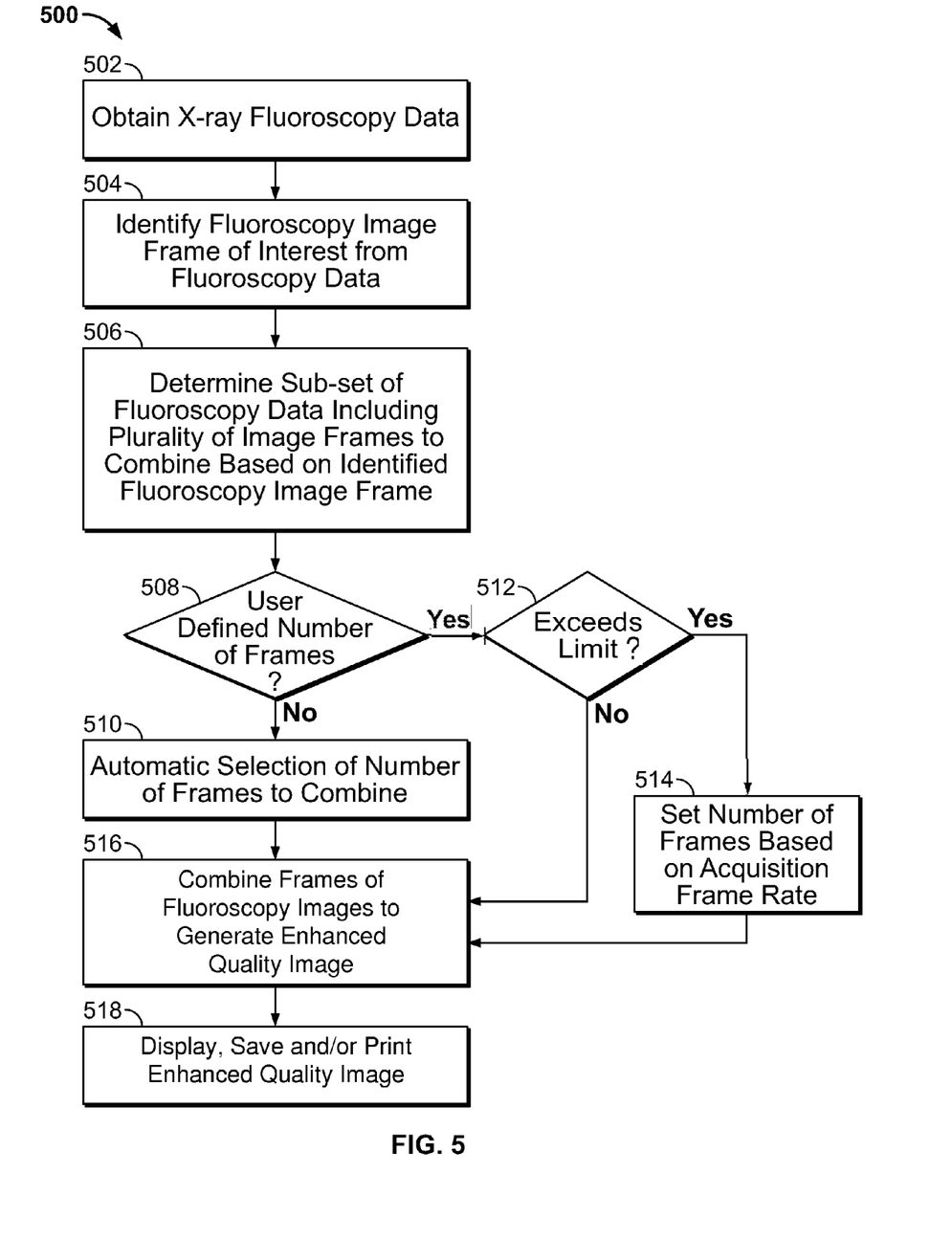
FIG. 5 is a flowchart of a method for enhancing and archiving x-ray images in accordance with various embodiments of the invention.

In accordance with various embodiments, a method 500 for enhancing and archiving x-ray images, such as x-ray fluoroscopic images is shown in FIG. 5. The method 500 includes obtaining x-ray fluoroscopy data at 502. For example, a plurality of images or frames of x-ray fluoroscopic data may be obtained from a current imaging scan or from stored data acquired during a previous imaging scan. The x-ray fluoroscopy data generally includes a plurality of frames of data acquired using low dose x-ray scanning techniques as described in more detail herein. Thereafter or during fluoroscopy imaging scanning, one or more fluoroscopy image frames of interest from the fluoroscopy data are identified at 504. For example, during a fluoroscopy imaging scan or after a portion or a complete fluoroscopy imaging scan has been performed and the fluoroscopy data stored, a user may identify a single frame of interest. The single frame of interest may be selected by a user, for example, based on possibly clinically relevant information in the frame of interest. The user may have viewed, for example, a portion or region of interest having a contrast dye imaged therewith. It should be noted that although some embodiments herein are described in connection with selecting a single frame, multiple frames may be selected with similar processing performed with respect to each selected frame.

Figure 6:
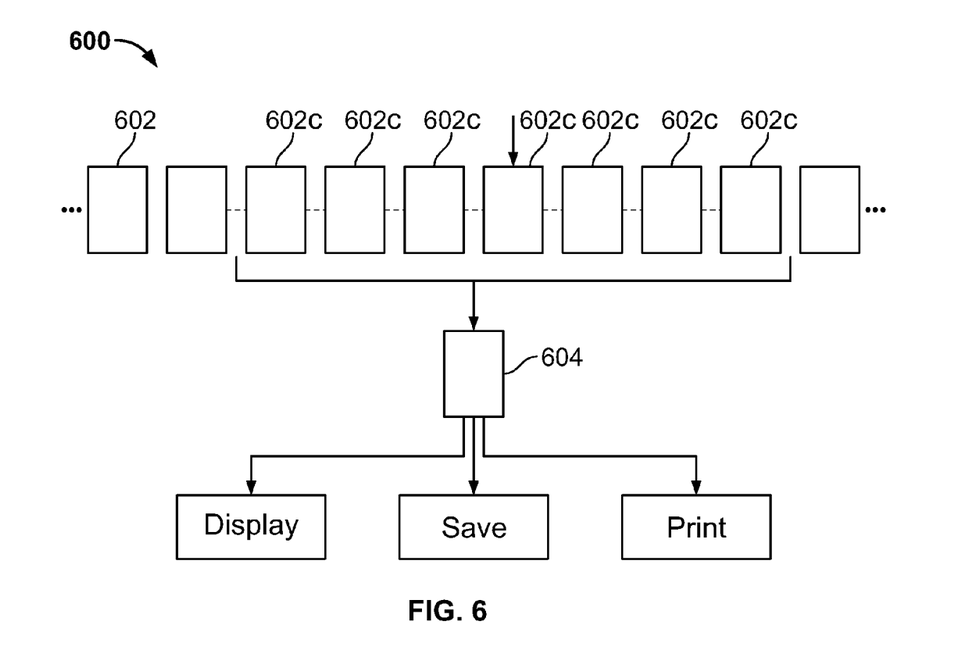
FIG. 6 is block diagram illustrating an image frame combination process performed in accordance with various embodiments of the invention.

It should be noted that during a scan or during a review of stored data corresponding to a scan, a user may select more than one single frame of interest. For example, several single frames of interest may be selected by a user. After one or more single frames of interest have been selected, a determination is made at 506 as to a subset of fluoroscopy data, which may be currently acquired, previously acquired and stored, or a combination thereof, to combine based on the one or more single fluoroscopy image frames. For example, as shown in FIG. 6, an image frame combination process 600 is performed. Specifically, from a plurality of image frames 602 that are being acquired or have been stored, a single image frame 602s (identified by an arrow), for example, a fluoroscopic image frame of interest is selected by a user. The image frame may be selected with a user input device (e.g., mouse) in real-time or retrospectively. Based on the selected single image frame 602s, a plurality of image frames 602c defining a subset of the fluoroscopy data are identified for combination, which includes the selected single image frame 602s. The subset of the fluoroscopy data is illustrated by the bracket under the image frames 602c and 602s.

Referring again to the method 500, after the subset of the fluoroscopy data is identified, a determination is made at 508 as to whether the subset is based on a user defined number of images frames, which may be configurable. For example, a user may predefine or select in realtime, a number of image frames to combine. If the identified subset of fluoroscopy data is not based on a user defined number of image frames, then at 510 the number of image frames is selected automatically. For example, the number of image frames may be automatically selected based on the acquisition rate of the fluoroscopy scan. In particular, the number of image frames selected is lower for a lower acquisition rate and higher for a higher acquisition rate.

If the identified subset of fluoroscopy data is based on a user defined number of image frames, then at 512, a determination is made as to whether the user defined number of image frames to combine exceeds a determined or predefined limit. For example, a determination is made as to whether the user defined or selected number of image frames is too high based on an acquisition frame rate of the fluoroscopic imaging system. If the user defined value for the number of image frames does exceed the limit, then at 514 the number of image frames to combine is reset. For example, the number of image frames to combine may be reset based on a current acquisition rate of the fluoroscopic imaging system. When the number of image frames to combine is reset, an indication may be provided, for example, a visual or audible indication to a user.

After the automatic selection of the number of image frames at 510, or if the user defined number of image frames is determined to not exceed the limit at 512 of if the user defined number of image frames is reset at 514, the image frames are combined at 516. In particular, a plurality of fluoroscopy image frames are combined such that a single enhanced or higher quality image, for example, an enhanced fluoroscopic image 604 (as shown in FIG. 6) is generated, such as an image having reduced image noise. For example, image correction or motion correction may be performed and then the selected image frames 602c (shown in FIG. 6) combined. In some embodiments, gross motion correction is first performed using any known process. For example, correction for gross image misalignment due to detector panning motion as is known may be performed. Thereafter, image-based registration to correct for motion also may be performed. For example, anatomical landmarks in the selected image frames 602c may be compared to adjust the orientation of the various images to perform more precise or fine image correction. It should be noted that any type of image registration technique to correct for patient movements (e.g., fine patient movements), such as patient movement related image differences may be performed. In some embodiments, for example, after performing gross image correction, fast image information (correlation) based registration techniques as are known may be used. It also should be noted that the image and motion correction may not be performed in some embodiments.

The selected image frames 602c are combined to form the enhanced fluoroscopic image 604 using different methods. For example, the selected image frames 602c may be combined using any known averaging technique. Optionally, a weighted averaging of the selected image frames 602c may be performed. For example, each of the selected image frames 602c may be given a weight based on different imaging characteristics as are known.

Figure 7:
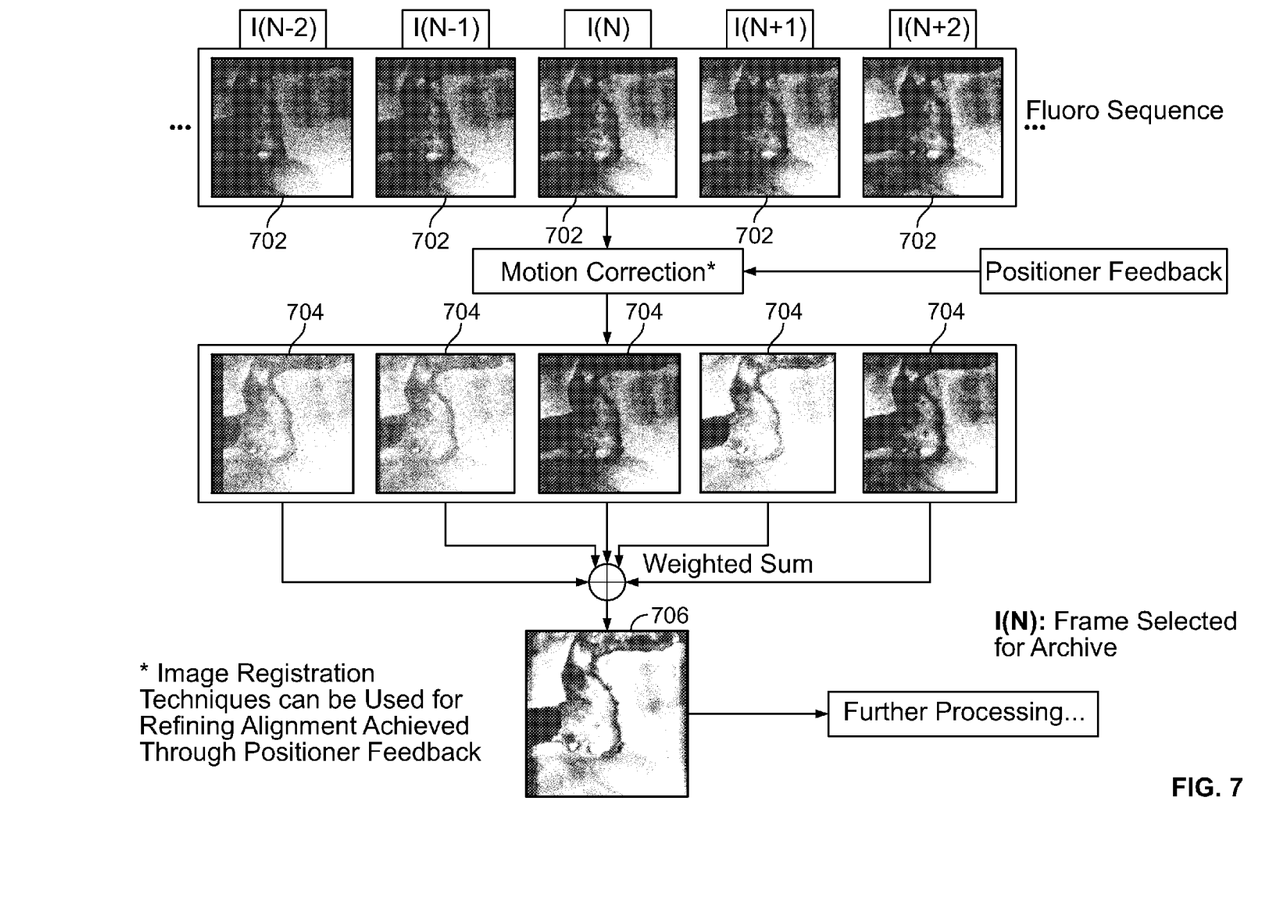
FIG. 7 is block diagram illustrating an enhanced fluoroscopic image generation process performed in accordance with various embodiments of the invention.

Thus, as shown in FIG. 7, an enhanced fluoroscopic image generation process 700 includes selecting a plurality of fluoroscopic image frames 702 defining a subset of a fluoro sequence. The fluoroscopic image frames 702 are corrected, for example, motion corrected, which may include using a positioner feedback to refine the image alignment. Thereafter, a plurality of motion corrected image frames 704 are combined, which may be a weighted combination, to form an enhanced fluoroscopic image 706. Thereafter, additional processing may be performed, such as other filtering techniques as is known.

Referring again to the method 500 shown in FIG. 5, after the fluoroscopy image frames are combined to generate the enhanced fluoroscopic image, for example, an enhanced quality image, the enhanced fluoroscopic image may be displayed, saved/archived and/or printed, among other functions, at 518 and also as shown in FIG. 6. If the enhanced fluoroscopic image is displayed, the enhanced fluoroscopic image may be displayed in combination with, for example, on the same screen as other non-enhanced fluoroscopic images, on a separate screen or instead of the non-enhanced fluoroscopic images. Also, it should be noted that a quality indicator of the image enhancement based on the motion correction may be displayed. For example, an indication may be displayed as to the type of motion correction performed, the number of image frames combined, etc. As another example, the quality indicator may correspond to a level of confidence in registration accuracy, level of detected motion, etc.

Figure 8:
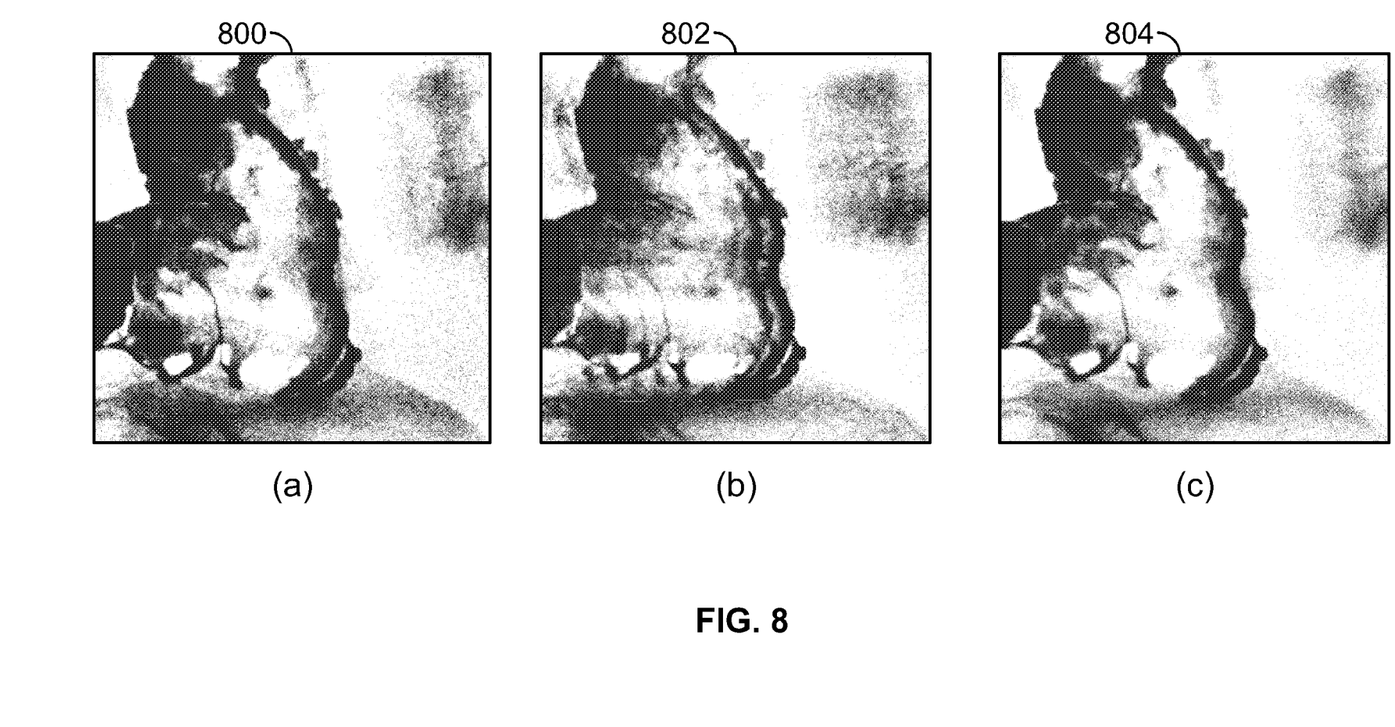
FIG. 8 are images illustrating different image enhancements resulting from methods performed in accordance with various embodiments of the invention.

Thus, as shown in FIG. 8, an original fluoroscopic image 800 acquired using a low dose scan is illustrated wherein there is noticeable visible noise. The image 802 illustrates an enhanced fluoroscopic image with only temporal accumulation performed in accordance with various embodiments wherein there is some noticeable motion-induced image lag artifact. The image 804 illustrates an enhanced fluoroscopic image with motion-corrected temporal accumulation performed in accordance with various embodiments wherein there is noticeable reduced noise without the appearance of image lag.

Figure 9:
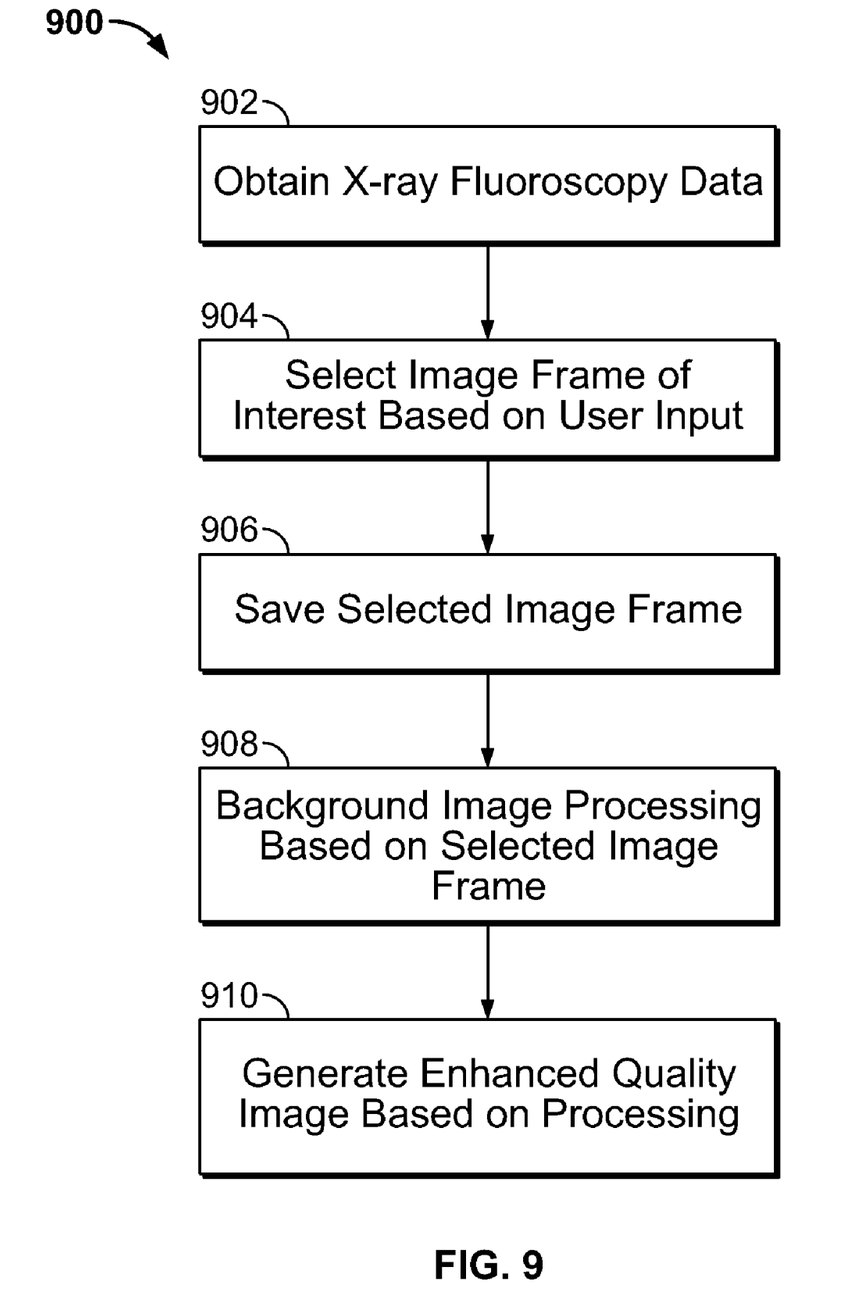
FIG. 9 is a flowchart of a method for background processing of x-ray images based a user defined image frame in accordance with various embodiments of the invention.

It should be noted that various embodiments the invention may also provide a method 900 as shown in FIG. 9 for background processing of x-ray images based a user defined image frame. In particular x-ray fluoroscopy data is obtained at 902, which may include realtime acquisition of fluoroscopic data. However, method 900 is not limited to being performed during realtime acquisition, but optionally may be performed during retrospective access of fluoroscopy data. Thereafter, a user selects an image frame at 904, which in various embodiments is selected during image acquisition. For example, as described in more detail herein, a user may select a single fluoroscopic image frame of interest, for example, one that appears to contain clinically relevant information while imaging a patient. Thereafter, the selected image frame is saved/archived at 906. Background image processing then may be performed at 908. The background image processing may include generating an enhanced fluoroscopic image as described herein, which may include generating an enhanced quality image at 910 based on the processing.

Thus, temporal image accumulation/averaging of fluoroscopic images that have been motion corrected is provided by the various embodiments. As a result, improved image quality is provided with less noise and less lag. This improved image quality provides image archiving at low fluoroscopy doses, which precludes or reduces the need for additional RAD exposures.

Thus, different workflow options can be implemented in connection with the image-processing methods and as described herein. For example, the system may accumulate the last N frames of fluoroscopy sequence to create 'LIH' image, where N=number of images to accumulate based on a user-preference or automatically based on a fluoroscopy acquisition frame rate. A "Record" button may be provided that initiates a special mode that processes multiple (N) low dose, high frame rate fluoroscopy frames (instead of single high dose record exposure) as described herein. Image processing is performed to enhance accumulated fluoroscopic images with improved image quality useful for patient records/diagnosis. A radiologist also can review a fluoroscopic image sequence retrospectively and select an image frame of interest.

Accordingly, increased flexibility to a user is provided to, for example, retrospectively select images for archive (Preferred Image Hold). By being able to select key frames of interest retrospectively from the entire fluoroscopy sequence or a portion thereof, a user (e.g., a radiologist) can complete an exam faster, because the user does not need to switch between fluoroscopy and record modes to save images, and does not need to repeat the procedure if some clinical scenarios are not captured in the images. The overall radiation dose is thereby reduced to the patient and the user and efficiency may be increased.

Some embodiments of the present invention provide a machine-readable medium or media having instructions recorded thereon for a processor or computer to operate an imaging apparatus to perform one or more embodiments of the methods described herein. The medium or media may be any type of CD-ROM, DVD, floppy disk, hard disk, optical disk, flash RAM drive, or other type of computer-readable medium or a combination thereof.

The various embodiments and/or components, for example, the processors, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for enhancing x-ray images, the method comprising:
   obtaining x-ray fluoroscopy data comprising a plurality of image frames; and
   performing image enhancement, including motion correction, on a subset of the acquired plurality of x-ray fluoroscopy image frames and generating a single enhanced x-ray image by combining the subset of the acquired plurality of x-ray fluoroscopy image frames, wherein a number of image frames included within the subset is one of user defined or automatically defined based on an acquisition rate for the obtained x-ray fluoroscopy data.

2. A method in accordance with claim 1 wherein performing motion correction includes using position and motion feedback information from system hardware during data acquisition.

3. A method in accordance with claim 1 wherein performing motion correction includes using image-based information.

4. A method in accordance with claim 1 wherein performing the image enhancement includes averaging at least some of the plurality of motion-corrected x-ray fluoroscopy image frames.

5. A method in accordance with claim 1 wherein performing the image enhancement includes performing a weighted temporal filtering of at least some of the plurality of motion-corrected x-ray fluoroscopy image frames.

6. A method in accordance with claim 1 wherein the subset of the acquired plurality of x-ray fluoroscopy image frames comprises a predetermined number of image frames immediately before and immediately after a user selected image frame.

7. A method in accordance with claim 1 wherein the motion correction comprises performing correction for a gross image misalignment due to detector panning motion and an image correction for patient motion.

8. A method for enhancing and archiving x-ray images, the method comprising:
   obtaining x-ray fluoroscopy data comprising a plurality of image frames;
   identifying at least one of the x-ray fluoroscopy image frames for enhancement based on a user input selecting at least one image frame of the plurality of image frames; and
   performing image enhancement, including motion-correction, on a subset of the x-ray fluoroscopy image frames, including the user identified image frame, to generate a single enhanced x-ray image corresponding to each of the identified x-ray fluoroscopy image frames, wherein the motion-correction comprises performing correction for a gross image misalignment due to detector panning motion and an image correction for patient motion.

9. A method in accordance with claim 8 wherein the user input defines, during the fluoroscopy image acquisition, the selected image frame.

10. A method in accordance with claim 9 further comprising performing background processing to generate an enhanced fluoroscopy image based on the user input during the fluoroscopy image acquisition.

11. A method in accordance with claim 8 wherein the user input defines, after the fluoroscopy image acquisition, the selected image frame using stored fluoroscopy images.

12. A method in accordance with claim 8 wherein performing image enhancement based on motion correction comprises using a configurable number of the plurality of image frames.

13. A method in accordance with claim 8 wherein the plurality of image frames used for image enhancement is a configurable number from a user input defining a number of image frames in the subset for combining to generate the single enhanced x-ray image.

14. A method in accordance with claim 8 wherein the plurality of image frames used for image enhancement is a configurable number based on a fluoroscopy image acquisition frame rate.

15. A method in accordance with claim 8 wherein the plurality of image frames used for image enhancement is a configurable number defined by a user input and further comprising adjusting the user defined number based on a fluoroscopy image acquisition frame rate if the configurable number defined by the user input exceeds a determined limit.

16. A method in accordance with claim 15 further comprising providing an indication of the adjustment.

17. A method in accordance with claim 8 further comprising displaying a quality indicator of the image enhancement based on the motion correction.

18. An x-ray fluoroscopy imaging system comprising:
an x-ray generator configured to generate and emit low dose x-rays;
an x-ray detector configured to detect low dose x-rays emitted from the x-ray generator after passing through an object to generate low dose x-ray fluoroscopy data;
a memory for storing the low dose x-ray fluoroscopy data from the x-ray detector; and
an image enhancement module configured to generate an enhanced x-ray image using motion correction on a subset of the acquired fluoroscopy image data, the enhanced x-ray image generated by combining the subset of the acquired fluoroscopy image data, a number of image frames in the subset selected one of (i) automatically based on an acquisition rate for the low dose x-ray fluoroscopy data or (ii) based on a user input selecting a number of image frames.

19. An x-ray fluoroscopy imaging system in accordance with claim 18 the acquired fluoroscopy image data used to generate the enhanced image comprises a plurality of frames based on a configurable number defined by the user input.

20. An x-ray fluoroscopy imaging system in accordance with claim 18 the acquired fluoroscopy image data used to generate the enhanced image comprises a plurality of frames based on a configurable number based defined by a fluoroscopy image acquisition frame rate.

21. An x-ray fluoroscopy imaging system in accordance with claim 18 wherein the image enhancement module is configured to perform motion correction using some of the acquired fluoroscopy image data to generate the enhanced x-ray image.

22. An x-ray fluoroscopy imaging system in accordance with claim 21 wherein the image enhancement module is configured to perform at least one of (i) averaging of and (ii) weighted temporal filtering of some of the plurality of motion corrected fluoroscopy image data.

* * * * *